US009632098B2

(12) United States Patent
Zeng et al.

(10) Patent No.: US 9,632,098 B2
(45) Date of Patent: Apr. 25, 2017

(54) MOESIN FRAGMENTS AND USES THEREOF

(75) Inventors: Xiaofeng Zeng, Shanghai (CN); Yue Zhang, Shanghai (CN); Zhinan Shou, Shanghai (CN); Hua Mao, Shanghai (CN); Hongbin Sun, Shanghai (CN); Jie Qian, Shanghai (CN); Yongjun Han, Shanghai (CN); Weina Situ, Shanghai (CN)

(73) Assignee: SHANGHAI KEXIN BIOTECH CO., LTD., Shanghai (CN)

( * ) Notice: Subject to any disclaimer, the term of this patent is extended or adjusted under 35 U.S.C. 154(b) by 889 days.

(21) Appl. No.: 13/878,230

(22) PCT Filed: Oct. 8, 2011

(86) PCT No.: PCT/CN2011/080519
§ 371 (c)(1),
(2), (4) Date: Apr. 8, 2013

(87) PCT Pub. No.: WO2012/045273
PCT Pub. Date: Apr. 12, 2012

(65) Prior Publication Data
US 2013/0210678 A1    Aug. 15, 2013

(30) Foreign Application Priority Data

Oct. 8, 2010  (WO) ................ PCT/CN2010/077587

(51) Int. Cl.
G01N 33/68     (2006.01)
C07K 14/705    (2006.01)
C07K 14/52     (2006.01)
C07K 16/18     (2006.01)
G01N 33/564    (2006.01)
A61K 38/19     (2006.01)

(52) U.S. Cl.
CPC ......... *G01N 33/6893* (2013.01); *C07K 14/52* (2013.01); *C07K 14/705* (2013.01); *C07K 16/18* (2013.01); *G01N 33/564* (2013.01); *G01N 33/6854* (2013.01); *A61K 38/19* (2013.01); *G01N 2800/52* (2013.01)

(58) Field of Classification Search
None
See application file for complete search history.

(56) References Cited

U.S. PATENT DOCUMENTS

| 5,976,810 | A  | 11/1999 | Wagatsuma et al. |
| 6,225,442 | B1 | 5/2001  | Wagatsuma et al. |
| 2013/0203091 | A1 | 8/2013  | Zhang et al. |
| 2013/0244259 | A1 | 9/2013  | Suzuki et al. |
| 2013/0266537 | A1 | 10/2013 | Zhang et al. |
| 2013/0316379 | A1 | 11/2013 | Zhang et al. |

FOREIGN PATENT DOCUMENTS

| CA | 2199498 A1    | 3/1996  |
| JP | 3467040 B     | 8/2003  |
| JP | 3735676 B1    | 1/2006  |
| JP | 2014-503467 A | 2/2014  |
| WO | 9607914 A1    | 3/1996  |
| WO | 2006015079 A2 | 2/2006  |
| WO | 2008122789 A2 | 10/2008 |
| WO | 2012045273 A1 | 4/2012  |
| WO | 2012045274 A1 | 4/2012  |
| WO | 2012045275 A1 | 4/2012  |
| WO | 2012045279 A1 | 4/2012  |

OTHER PUBLICATIONS

Waiker et al (J Am Soc Nephrol. Jan. 2012; 23(1): 13-21).*
Castro et al (J Allergy Clin Immunol. Feb. 2010 ; 125(2 Suppl 2): S238-S247).*
Espinoza et al., "Anti-moesin antibodies derived from patients with aplastic anemia stimulate monocytic cells to secrete TNF-a through an ERK1/2-dependent pathway" Intl. Immu. 21 (8): 913-923 (2009).
Lankes et al., "A heparin-binding protein involved in inhibition of smooth-muscle cell proliferation" Biochem J. 251:831-842 (1988).
Louvet-Vallee, "ERM proteins: From cellular architecture to cell signaling" Biol. Cell 92:305-316 (2000).
Takamatsu et al., "Specific antibodies to moesin, a membrane-cytoskeleton linker protein, are frequently detected in patients with acquired aplastic anemia" Blood 109 (6):2514-2520 (2007).
Takamatsu et al., "Anti-Moesin Antibodies in the Serum of Patients with Aplastic Anemia Stimulate Peripheral Blood Mononuclear Cells to Secrete TNF-α and IFN-γ" J. Immunol. 182:703-710 (2009).
Wagatsuma et al., "Ezrin, radixin and moesin are possible autoimmune antigens in rheumatoid arthritis" Mol. Immuol., 33 (15):1171-1176 (1996).
Edwards et al., "The 2.7 Å Crystal Structure of the Activated FERM Domain of Moesin: An Analysis of Structural Changes on Activation" Biochemistry 40: 7061-7068 (2001).
Finnerty et al., "The EBP50-moesin interaction involves a binding site regulated by direct masking on the FERM domain" J. Cell Science 117:1547-1552 (2004).
"ISR and Written Opinion of PCT CN2011/080519", Date of mailing: Jan. 19, 2012.
ZhaoJiuLiang "Study on Anti-moesin Antibodies in Patients with Connective Tissue Diseases" 2009.

(Continued)

*Primary Examiner* — Brian J Gangle
*Assistant Examiner* — Andrea McCollum
(74) *Attorney, Agent, or Firm* — Jun He Law Offices P.C.; Zhaohui Wang

(57) ABSTRACT

The present application provides compositions and methods useful for detecting and monitoring autoimmune diseases in a human subject. The methods comprise providing a moesin fragment for binding to an anti-moesin autoantibody and contacting the moesin fragment with a sample obtained from the human subject. The moesin fragment comprises the entire N-terminal FERM domain of a human moesin protein. The human subject has or is suspected of having an autoimmune disease such as connective tissue disease, systemic sclerosis, Sjogren's syndrome, or systemic lupus erythematosus.

9 Claims, 5 Drawing Sheets

(56) References Cited

OTHER PUBLICATIONS

"International Search Report for PCT/CN2011/080520", Date of Mailing: Jan. 19, 2012.

Hipfner et al., "Slik Sterile-20 kinase regulates Moesin activity to promote epithelial integrity during tissue growth" Genes Dev. 18:2243-2248 (2004).

Pearson et al., "Structure of the ERM Protein Moesin Reveals the FERM Domain Fold Masked by an Extended Actin Binding Tail Domain" Cell 101:259-270 (2000).

Sato et al., "A gene family consisting of ezrin, radixin and moesin. Its specific localization at actin filament/plasma membrane association sites" J. Cell Sci. 103:131-143 (1992).

Oshiro et al., "Phosphorylation of Moesin by Rho-associated Kinase (Rho-kinase) Plays a Crucial Role in the Formation of Microvilli-like Structures" J. Biol. Chem. 273:34663-34666 (1998).

Takahashi et al., "Direct Interaction of the Rho GDP Dissociation Inhibitor with Ezrin/Radixin/Moesin Initiates the Activation of the Rho Small G Protein" J. Biol. Chem. 272:23371-23375 (1997).

Tohme et al., "Moesin Functions as a Lipopolysaccharide Receptor on Human Monocytes" Infect. Immun. 67(7):3215-3220 (1999).

Jeon Songhee et al.:"RhoA and Rho Kinase-dependent Phosphorylation of Moesin at Thr-558 in Hippocampal Neuronal Cells by Glutamate" J.Biol. Chern 277: 16576-16584 (2002).

Martin Hennenberg et al.: "Intrahepatic Hyperphosphorylation of the Rho-Kinase-Substrate Moesin in Experimental and Human Cirrhosis" Gastroenterolofy, vol. 130, No. 4, Suppl. 2, p. A669, XP009175910, (2006).

Okayama Tohunari et al.:"Attenuated response to liver injury in moesin-deficient mice: Impaired stellate cell migration and decreased fibrosis" BIO 1782: 542-548 (2008).

Alissa Routhier et al.: "Pharmacological inhibition of Rho-kinase signaling with Y-27632 blocks melanoma tumor growth" Oncology Reports 23: 861-867 (2010).

Ana Estecha et al.: "Moesin orchestrates cortical polarity of melanoma tumour cells to initiate 3D invasion" Journal of Cell Science 122: 3492-3501 (2009).

Young et al., "Current concepts in the pathophysiology and treatment of aplastic anemia" Blood, 108:2509-2519 (2006).

Pang Yan et al., "Study on the expression of interferon-gamma and tumor necrosis factor-α in peripheral blood of patients with chronic aplastic anemia" Journal of Clinical Hematology, 23 (7): 416-418 (Jul. 2010).

Shcherbina et al., "Moesin, the major ERM protein of lymphocytes and platelets, differs from ezrin in its insensitivity to calpain" FEBS Letters 443:31-36 (1999).

"ISR and Written Opinion of PCT CN2011/080523", Date of Mailing: Jan. 19, 2012.

"ISR and Written Opinion of PCT CN2011/080532", Date of Mailing: Jan. 19, 2012.

Yue Zhang et al., "Autoantibodies Directed Against Moesin C471-577/N1-297 Are Novel and Specific Biomarkers of Immune Thrombocytopenic Purpura (ITP)" (2011).

Hiroyuki Takamatsu, et al., "Anti-Moesin Antibodies in the Serum of Patients with Aplastic Anemia Stimulate Peripheral Blood Mononuclear Cells to Secrete INF− and IFN−" (2009).

Alarcon-Segovia, D. et al., "Antiphospholipid antibodies and the antiphospholipid syndrome in systemic lupus erythematosus. A prospective analysis of 500 consecutive patients" Medicine 68 (6): 353-365 (1989).

Asherson, R.A., et al., "The "Primary" Antiphospholipid Syndrome: Major Clinical and Serological Features" Medicine 68 (6): 366-374 (1989).

Nakamura Fumihiko et al., "Phosphorylation of Threonine 558 in the Carboxyl-terminal Actin-binding Domain of Moesin by Thrombin Activation of Human Platelets" Biological Chemistry 270: 52(1995).

"ISR and Written Opinion of PCT CN2011/080538" Date of Mailing: Jan. 19, 2012.

Zhirong Qi et al.: "Antoantibodies specific to hnRNP K: a new diagnostic marker for immune pathophysiology in aplastic anemia" Ann Hematol 89: 1255-1263 (2010).

Pedro L et al.: "Development of a high-throughout AlphaScreen assay measuring full-length LRRK2(G2019S) kinase activity using moesin protein substrate" Analytical Biochemistry 404: 45-51 (2010).

\* cited by examiner

DRAWINGS

Amino Acid Sequence of the Full Length Human Moesin Protein (Moesin-5)

MPKTISVRVTTMDAELEFAIQPNTTGKQLFDQVVKTIGLREVWFFGLQYQDTKGFSTWL
KLNKKVTAQDVRKESPLLFKFRAKFYPEDVSEELIQDITQRLFFLQVKEGILNDDIYCPPE
TAVLLASYAVQSKYGDFNKEVHKSGYLAGDKLLPQRVLEQHKLNKDQWEERIQVWHE
EHRGMLREDAVLEYLKIAQDLEMYGVNYFSIKNKKGSELWLGVDALGLNIYEQNDRLT
PKIGFPWSEIRNISFNDKKFVIKPIDKKAPDFVFYAPRLRINKRILALCMGNHELYMRRRK
PDTIEVQQMKAQAREEKHQKQMERAMLENEKKKREMAEKEKEKIEREKEELMERLKQI
EEQTKKAQQELEEQTRRALELEQERKRAQSEAEKLAKERQEAEEAKEALLQASRDQKK
TQEQLALEMAELTARISQLEMARQKKESEAVEWQQKAQMVQEDLEKTRAELKTAMST
PHVAEPAENEQDEQDENGAEASADLRADAMAKDRSEEERTTEAEKNERVQKHLKALTS
ELANARDESKKTANDMIHAENMRLGRDKYKTLRQIRQGNTKQRIDEFESM (SEQ ID
NO:1)

Figure 1

Moesin-1:   1-297 aa (N-terminal FERM domain of the human moesin protein)

MPKTISVRVTTMDAELEFAIQPNTTGKQLFDQVVKTIGLREVWFFGLQYQDTKGFSTWL
KLNKKVTAQDVRKESPLLFKFRAKFYPEDVSEELIQDITQRLFFLQVKEGILNDDIYCPPE
TAVLLASYAVQSKYGDFNKEVHKSGYLAGDKLLPQRVLEQHKLNKDQWEERIQVWHE
EHRGMLREDAVLEYLKIAQDLEMYGVNYFSIKNKKGSELWLGVDALGLNIYEQNDRLT
PKIGFPWSEIRNISFNDKKFVIKPIDKKAPDFVFYAPRLRINKRILALCMGNHELYMRRRK
P (SEQ ID NO:2)

Moesin-2:   298-577 aa (helical and C-terminal tail domains of the human moesin protein)

DTIEVQQMKAQAREEKHQKQMERAMLENEKKKREMAEKEKEKIEREKEELMERLKQI
EEQTKKAQQELEEQTRRALELEQERKRAQSEAEKLAKERQEAEEAKEALLQASRDQKK
TQEQLALEMAELTARISQLEMARQKKESEAVEWQQKAQMVQEDLEKTRAELKTAMST
PHVAEPAENEQDEQDENGAEASADLRADAMAKDRSEEERTTEAEKNERVQKHLKALTS
ELANARDESKKTANDMIHAENMRLGRDKYKTLRQIRQGNTKQRIDEFESM (SEQ ID
NO:3)

Moesin-3:   298-470 aa (helical domain of the human moesin protein)

DTIEVQQMKAQAREEKHQKQMERAMLENEKKKREMAEKEKEKIEREKEELMERLKQI
EEQTKKAQQELEEQTRRALELEQERKRAQSEAEKLAKERQEAEEAKEALLQASRDQKK
TQEQLALEMAELTARISQLEMARQKKESEAVEWQQKAQMVQEDLEKTRAELKTAMST
P (SEQ ID NO:4)

Moesin-4:   471-577 aa (C-terminal tail domain of the human moesin protein)

HVAEPAENEQDEQDENGAEASADLRADAMAKDRSEEERTTEAEKNERVQKHLKALTS
ELANARDESKKTANDMIHAENMRLGRDKYKTLRQIRQGNTKQRIDEFESM (SEQ ID
NO:5)

Figure 2 cDNA Sequence encoding for the Full Length Human Moesin Protein

ATGCCCAAAACGATCAGTGTGCGTGTGACCACCATGGATGCAGAGCTGGAGTTTGCCATCCAGC
CCAACACCACCGGGAAGCAGCTATTTGACCAGGTGGTGAAAACTATTGGCTTGAGGGAAGTTTG
GTTCTTTGGTCTGCAGTACCAGGACACTAAAGGTTTCTCCACCTGGCTGAAACTCAATAAGAAG
GTGACTGCCCAGGATGTGCGGAAGGAAAGCCCCTGCTCTTTAAGTTCCGTGCCAAGTTCTACC
CTGAGGATGTGTCCGAGGAATTGATTCAGGACATCACTCAGCGCCTGTTCTTTCTGCAAGTGAA
AGAGGGCATTCTCAATGATGATATTTACTGCCCGCCTGAGACCGCTGTGCTGCTGGCCTCGTAT
GCTGTCCAGTCTAAGTATGGCGACTTCAATAAGGAAGTGCATAAGTCTGGCTACCTGGCCGGAG
ACAAGTTGCTCCCGCAGAGAGTCCTGGAACAGCACAAACTCAACAAGGACCAGTGGGAGGAGCG
GATCCAGGTGTGGCATGAGGAACACCGTGGCATGCTCAGGGAGGATGCTGTCCTGGAATATCTG
AAGATTGCTCAAGATCTGGAGATGTATGGTGTGAACTACTTCAGCATCAAGAACAAGAAAGGCT
CAGAGCTGTGGCTGGGGGTGGATGCCCTGGGTCTCAACATCTATGAGCAGAATGACAGACTAAC
TCCCAAGATAGGCTTCCCCTGGAGTGAAATCAGGAACATCTCTTTCAATGATAAGAAATTTGTC
ATCAAGCCCATTGACAAAAAGCCCCGGACTTCGTCTTCTATGCTCCCCGGCTGCGGATTAACA
AGCGGATCTTGGCCTTGTGCATGGGGAACCATGAACTATACATGCGCCGTCGCAAGCCTGATAC
CATTGAGGTGCAGCAGATGAAGGCACAGGCCCGGGAGGAGAAGCACCAGAAGCAGATGGAGCGT
GCTATGCTGGAAAATGAGAAGAAGAAGCGTGAAATGGCAGAGAAGGAGAAAGAGAAGATTGAAC
GGGAGAAGGAGGAGCTGATGGAGAGGCTGAAGCAGATCGAGGAACAGACTAAGAAGGCTCAGCA
AGAACTGGAAGAACAGACCCGTAGGGCTCTGGAACTTGAGCAGGAACGGAAGCGTGCCCAGAGC
GAGGCTGAAAAGCTGGCCAAGGAGCGTCAAGAAGCTGAAGAGGCCAAGGAGGCCTTGCTGCAGG
CCTCCCGGGACCAGAAAAAGACTCAGGAACAGCTGGCCTTGGAAATGGCAGAGCTGACAGCTCG
AATCTCCCAGCTGGAGATGGCCCGACAGAAGAAGGAGAGTGAGGCTGTGGAGTGGCAGCAGAAG
GCCCAGATGGTACAGGAAGACTTGGAGAAGACCCGTGCTGAGCTGAAGACTGCCATGAGTACAC
CTCATGTGGCAGAGCCTGCTGAGAATGAGCAGGATGAGCAGGATGAGAATGGGGCAGAGGCTAG
TGCTGACCTACGGGCTGATGCTATGGCCAAGGACCGCAGTGAGGAGGAACGTACCACTGAGGCA
GAGAAGAATGAGCGTGTGCAGAAGCACCTGAAGGCCCTCACTTCGGAGCTGGCCAATGCCAGAG
ATGAGTCCAAGAAGACTGCCAATGACATGATCCATGCTGAGAACATGCGACTGGGCCGAGACAA
ATACAAGACCCTGCGCCAGATCCGGCAGGGCAACACCAAGCAGCGCATTGACGAATTTGAGTCT
ATGTAA (SEQ ID NO:6)

Figure 3 pET32a(+)

pET28a(+)

MOESIN FRAGMENTS AND USES THEREOF

CROSS REFERENCE

This application is a national phase stage of international application PCT/CN2011/080519, filed Oct. 08, 2011, which claims the priority to international application PCT/CN2010/077587filed Oct. 08, 2010, the disclosure of which is incorporated herein by reference in their entirety.

TECHNICAL FIELD

The present application relates generally to the diagnosis and treatments of autoimmune diseases. More specifically, the present application concerns methods and compositions based on presence and levels of antigen-specific autoantibodies associated with various aspects of autoimmune diseases.

BACKGROUND

Autoimmune diseases are diseases arising from aberrant response of the immune system against one's own substances and tissues. There are more than 80 different types of autoimmune diseases that, collectively, amount to the number two cause of chronic illness, and one of the top 10 leading causes of death in women of all age groups up to 64 years.

Significant medical research efforts have been devoted to understanding the mechanism of autoimmune diseases and finding effective diagnosis and treatments therefore. Many autoimmune diseases are now characterized by the presence and undesirable activities of autoantibodies. These autoantibodies recognize and bind to often normal and healthy self antigens, thereby causing significant damages and failures of relevant tissues and organs.

Many autoimmune antigens have been identified by immunoassays with sera from patients with autoimmune diseases. One of such target antigens is moesin—membrane-organizing extension spike protein, found to be reactive to autoantibodies in patients with rheumatoid arthritis (RA). Wagatsuma et al., Mol. Immuol., 33:1171-6 (1996). Moesin was initially identified in bovine uterus and characterized as a possible receptor for heparin. Lankes et al., Biochem J. 251:831-42 (1988). Further studies have characterized moesin as a member of the ezrin-radixin-moesin (ERM) protein family. These are proteins that are primarily expressed in cytoplasm, concentrated in actin rich cell-surface structures. They act as structural linkers between the plasma membrane and the actin cytoskeleton, playing roles in the formation of microvilli, cell-cell adhesion, maintenance of cell shape, cell mobility and membrane trafficking. Later studies have revealed that they are also involved in physiological and pathological signal transductions. Louvet-Vallee, Biol. Cell 92:305-16 (2000).

Sequence and structural analysis of the ERM proteins revealed that they share high degrees of inter-species and inter-molecular homologies. The ERM proteins have three domains: an N-terminal domain called FERM domain (band four-point-one, ezrin, radixin, moesin homology domain) because of its homology with the band 4.1 protein, a central helical domain and a C-terminal tail domain. The C-terminal tail domain binds F-actin while the N-terminal FERM domain is responsible for binding to adhesion molecules in the plasma membrane. Louvet-Vallee (2000).

Wagatsuma et al (1996) reported detections of anti-ERM autoantibodies in RA patients. Of the 71 patient sera tested, 24 samples (33.8%) reacted with at least one of the recombinant ERM antigens and 10 samples (14%) reacted with recombinant moesin alone. However, the study did not find significant correlation between the presence of anti-ERM antibodies and clinical manifestation, such as disease duration or stage. Moreover, sera from patients with other autoimmune diseases such as Primary Sojgren's Syndrome (PSS) and systemic lupus erythematosus (SLE) did not show any reactivity to the three ERM proteins.

Takamatsu et al reported detection of specific antibodies to moesin in the sera of patients with acquired aplastic anemia (AA). Takamatsu et al., Blood 109:2514-20 (2007). Using ELISA, anti-moesin antibodies were shown at high titers in 25 of 67 (37%) AA patients. Further in vitro studies showed that anti-moesin antibodies from AA patients induced inflammatory cytokines such as TNF-α and IFN-γ, implicating its role in the pathophysiology of the disease. Espinoza et al., Intl. Immu. 21:913-23 (2009); Takamatsu et al., J. Immunol. 182:703 (2009).

One of the challenges in clinical management of autoimmune diseases is the accurate and early identification of the diseases in a patient. To this end, it would be highly advantageous to have molecular-based diagnostic tools that can be used to objectively identify presence and/or extent of disease in a patient. The present application described herein provides these tools and other benefits.

DISCLOSURE OF THE INVENTION

The present application provides compositions and methods for diagnosing and monitoring autoimmune disorders based at least in part on the generation of moesin fragments from particular moesin functional domains and their uses for detecting anti-moesin autoantibodies in biological samples, whose presence and level in turn correlate with disease type and stage in patients with autoimmune disorders.

In one aspect, the present application provides a composition comprising a moesin fragment capable of binding to an anti-moesin autoantibody, wherein the moesin fragment comprises at least ten consecutive amino acid residues from a human moesin protein domain, wherein the human moesin protein domain is selected from the group consisting of the N-terminal FERM domain, the helical domain and the C-terminal tail domain of the human moesin protein, and wherein the moesin fragment is not a full length human moesin protein. In certain embodiments, the N-terminal FERM domain consists of amino acid residues 1-297 of the human moesin protein, the helical domain consists of amino acid residues 298-470 of the human moesin protein, and the C-terminal tail domain consists of amino acid residues 471-577 of the human moesin protein.

In certain embodiments, the moesin fragment of the present application comprises at least 10, 20, 30, 40, 50, 60, 70, 80, 90 or 100 consecutive amino acid residues of the N-terminal FERM domain, the helical domain or the C-terminal tail domain of the human moesin protein. In certain embodiments, the moesin fragment comprises at least 9, 10, 11, 12, 13, 14, 15, 16, 17, 18, 19, 20, 21, 22, 23, 24, 25, 26, 27, 28, 29 or 30 consecutive amino acid residues of the N-terminal FERM domain, the helical domain or the C-terminal tail domain of the human moesin protein.

In certain embodiments, the moesin fragment of the present application comprises at least ten consecutive amino acid residues from the region between amino acid residues 2-297, 3-297, 4-297, 1-294, 1-295, 1-296, 299-470, 300-470, 298-468, 298-469, 472-577, 473-577, 471-575 or 471-576 of the human moesin protein. In certain embodiments, the moesin fragment of the present application comprises at least ten consecutive amino acid residues from the region between amino acid residues 1-94, 95-201, 202-297, 471-478, 488-501 or 502-577 of the human moesin protein. In one embodiment, the moesin fragment comprises the entire N-terminal FERM domain of human moesin protein; in another embodiment, the moesin fragment comprises the entire helical and C-terminal tail domains of human moesin protein; in yet another embodiment, the moesin fragment comprises the entire helical domain of human moesin protein; in still another embodiment, the moesin fragment comprises the entire C-terminal tail domain of human moesin protein.

In certain embodiments, the moesin fragment of the present application consists essentially of the N-terminal FERM domain of the human moesin protein or a fragment thereof. In certain embodiments, the moesin fragment of the present application consists essentially of amino acid residues 1-297, 1-94, 95-201 or 202-297 of the human moesin protein or a fragment thereof. In certain embodiments, the moesin fragment of the present application consists essentially of the helical domain of the human moesin protein or a fragment thereof. In certain embodiments, the moesin fragment of the present application consists essentially of amino acid residues 298-470 of the human moesin protein or a fragment thereof. In certain embodiments, the moesin fragment of the present application consists essentially of the C-terminal tail domain of the human moesin protein or a fragment thereof. In certain embodiments, the moesin fragment of the present application consists essentially of amino acid residues 471-577, 471-478, 488-501 or 502-577 of the human moesin protein or a fragment thereof.

In certain embodiments, the moesin fragment of the present application comprises at least ten consecutive amino acids of the N-terminal FERM domain of the human moesin protein, wherein the moesin fragment does not contain any substantial portion of the helical domain and the C-terminal tail domain of the human moesin protein. As used herein the term "substantial portion" refers to a portion of the relevant domain (helical domain or N-terminal FERM domain or C-terminal tail domain) that can compete with such domain (helical domain or N-terminal FERM domain or C-terminal tail domain) for specific binding to an antibody capable of binding to the entire relevant domain (helical domain or N-terminal FERM domain or C-terminal tail domain).

In certain embodiments, the moesin fragment of the present application comprises at least ten consecutive amino acids of the helical domain of the human moesin protein, wherein the moesin fragment does not contain any substantial portion of the N-terminal FERM domain and the C-terminal tail domain of the human moesin protein.

In certain embodiments, the moesin fragment of the present application comprises at least ten consecutive amino acids of the C-terminal tail domain of the human moesin protein, wherein the moesin fragment does not contain any substantial portion of the N-terminal FERM domain and the helical domain of the human moesin protein.

In certain embodiments, the moesin fragment of the present application shares an amino acid sequence identify of at least 70%, 75%, 80%, 85%, 90%, 95%, 96%, 97%, 98%, or 99% with the N-terminal FERM domain of human moesin protein or a fragment thereof, or the helical domain of human moesin protein or a fragment thereof, or the C-terminal tail domain of the human moesin protein or a fragment thereof. In certain embodiments, the moesin fragment shares an amino acid sequence identify of at least 70%, 75%, 80%, 85%, 90%, 95%, 96%, 97%, 98%, or 99% with the amino acid sequence selected from the group consisting of amino acid residues 1-94, 95-201, 202-297, 471-478, 488-501 or 502-577 of the human moesin protein. In certain embodiments, the moesin fragment of the present application share an amino acid sequence identify of at least 70%, 75%, 80%, 85%, 90%, 95%, 96%, 97%, 98%, or 99% with the entire N-terminal FERM domain, or the entire helical domain, or the entire C-terminal tail domain of human moesin protein.

In certain embodiments, the moesin fragment of the present application further comprises a carrier polypeptide. The term "carrier polypeptide" refers to any peptide or polypeptide that can be conjugated to the moesin fragment of the present application. A carrier polypeptide can be beneficial to the peptide of the present application, e.g. to promote the stability, solubility, specific or non-specific binding affinity and/or function of the peptide of the present application. However, a carrier polypeptide is not required to provide any benefit or even biological function to the peptide of the present application. Commonly used carrier polypeptides includes, but not limited to, human serum albumin, bovine serum albumin, antibody fragments such as the antibody constant region.

In one aspect, the present application provides uses of the moesin fragment described herein or an antibody thereof in the manufacture of a diagnostic composition for detection of an anti-moesin autoantibody in a sample from a subject.

A sample can be any biological composition that is obtained or derived from a subject of interest that contains a cellular and/or other molecular entity that is to be characterized and/or identified, for example based on physical, biochemical, chemical and/or physiological characteristics. In certain embodiments, the sample is a blood sample comprising whole blood, serum or plasma obtained from a subject. A subject can be a human or an animal subject. In certain aspects, the human subject has or is suspected of having an autoimmune disorder, such as connective tissue disease (CTD), systemic sclerosis, Sjogren's Syndrome, rheumatoid arthritis, and systemic Lupus erythematosus. In one aspect, the CTD is associated with pulmonary complications such as, but not limited to, pulmonary arterial hypertension (PAH), interstitial lung disease (ILD), lung fibrosis, chronic obstructive pulmonary disease, bronchiectasis and lung infection. Detection can be conducted in vitro, in vivo or ex vivo.

In one aspect, the autoimmune disorder to be diagnosed by the present application is associated with abnormal epithelial cells or abnormal vascular endothelial cells. In certain embodiments, the disease-associated epithelial cells or vascular endothelial cells undergo abnormal proliferation; in other embodiments, these cells undergo abnormal apoptosis. In some other aspects, the autoimmune disorder to be diagnosed by the present application is associated with fibrosis of tissues or organs of the subject.

In one aspect, autoantibody can be detected in a number of ways, such as by Western blotting and ELISA procedures for assaying a wide variety of tissues and samples, including plasma or serum. A wide range of immunoassay techniques using such an assay format are available. These include both single-site and two-site or "sandwich" assays of the non-competitive types, as well as in the traditional competitive binding assays. These assays also include direct binding of a labeled antigen to target autoantibodies.

In one aspect, the present application provides an antibody detection panel for detecting anti-moesin autoantibody in a sample, said antibody detection panel comprising a moesin fragment and a substrate upon which the moesin fragment is immobilized. In one aspect, the substrate is a solid phase. In one embodiment, the antibody detection panel of the present application comprises two moesin fragments that represent two different moesin domains for the purpose of calculating and comparing relative differences in autoantibody levels for different moesin domains. In another embodiment, the antibody detection panel of the present application comprises three moesin fragments representing the three different moesin domains (N-terminal FERM domain, helical domain, C-terminal tail domain) for calculating relative differences in autoantibody levels. The antibody detection panels of the present application can be made into detection kits along with instructions for how to use the detection panels.

In one aspect, the antibody detection panel further comprises a secondary antibody as a detecting agent capable of binding to anti-moesin autoantibodies. In some embodiments, the secondary antibody is chemically labeled. Many antibodies can be used as a secondary antibody, such as a goat-anti human IgG. In another aspect, autoantibody can be detected without using a secondary antibody as detecting agent. Many known techniques for direct detection of antigen-antibody bindings are available and can be used to practice the present application.

In one aspect, the present application provides an anti-moesin antibody capable of binding to the moesin fragment as described above. Such antibody is capable of competing with moesin autoantibodies for binding to a specific moesin fragment in a subject. Such antibody can be used in a competition binding assay, wherein the reduction of binding signals can be indicative of the presence and level of the corresponding autoantibodies.

In one aspect, the present application provides a method of detecting an anti-moesin autoantibody in a sample, comprising contacting a moesin fragment as described above with the sample to allow antigen-antibody binding, and detecting the antibody binding to the moesin fragment.

In one aspect, the present application provides a method of diagnosing an autoimmune disorder in a subject, comprising contacting a moesin fragment as described above with a sample obtained from the subject under antigen-antibody binding conditions and determining whether the anti-moesin autoantibody level of the sample is significantly greater than that of a normal reference sample, thereby indicating that the subject has an autoimmune disorder.

In one aspect, the present application provides a method of detecting an anti-moesin autoantibody in a sample, comprising contacting a first moesin fragment and a second moesin fragment as described above with the sample to allow antigen-antibody binding to the first moesin fragment and the second moesin fragment, respectively, and detecting the antibody binding to the those moesin fragments, wherein the first and second moesin fragments comprise amino acids sequences from different domains of the human moesin protein. The different levels of the anti-moesin autoantibodies binding to the first and second moesin fragments, respectively, may be correlated with the different stages and degrees of severity of an autoimmune disorder in a subject. In certain embodiments, the sample is tested for binding of the first moesin fragment to the anti-moesin antibodies before tested for binding of the second moesin fragment to the anti-moesin antibodies. In certain embodiments, the sample is tested for binding of the first and second moesin fragments to the anti-moesin antibodies at the same time. In certain embodiments, the sample is tested for binding of the first moesin fragment to the anti-moesin antibodies after tested for binding of the second moesin fragment to the anti-moesin antibodies, and then tested at higher concentration of the sample for binding of the second moesin fragment to the anti-moesin antibodies again.

In one aspect, the present application provides a method of detecting an anti-moesin autoantibody in a sample, comprising contacting a first, second and third moesin fragments as described above with the sample to allow antigen-antibody binding to the first, second and third moesin fragments, respectively, and detecting the antibody binding to the those moesin fragments, wherein the first, second and third moesin fragments comprise amino acids sequences from different domains of the human moesin protein. In certain embodiments, the sample is tested for binding of the first, second and third moesin fragments to the anti-moesin antibodies sequentially. In certain embodiments, the sample is tested for binding of the first, second and third moesin fragments to the anti-moesin antibodies at the same time.

In one aspect, the present application provides a method of determining the pathological state of a patient having an autoimmune disorder, comprising contacting under antigen-antibody binding conditions a moesin fragment as described above with a sample obtained from the patient; measuring the level of anti-moesin autoantibody reactive to the moesin fragment in the sample; and determining the pathological state of the patient according to a comparison of the anti-moesin autoantibody level to a reference database correlating anti-moesin autoantibody levels to pathological states of the autoimmune disorder.

In one embodiment, the present application provides a method of monitoring treatment progress in a patient undergoing an autoimmune disorder therapy, comprising contacting under antigen-antibody binding conditions a moesin fragment with a sample obtained from the patient; measuring the anti-moesin autoantibody level in said sample; and comparing the autoantibody level to that of a reference sample obtained from the same patient prior to the therapy, wherein a decrease in titer is indicative of positive response of the subject to the treatment.

In some embodiments, the present application provides methods of analyzing a sample obtained from a subject, comprising the following steps: a) providing an antibody detection panel as described above; b) contacting under antigen-antibody binding conditions the antibody detection panel with a sample; c) detecting any presence of anti-moesin autoantibodies in the sample; and d) measuring the anti-moesin autoantibody levels in step c). Optionally, the methods further comprise e) comparing the level from step d) to that of a reference sample or a reference database. In some aspects, the methods of analyzing samples according to the present application are used for purposes of disease diagnosis, disease progression, disease prognosis or treatment response. In one aspect, the subject can be a human patient having or suspected of having an autoimmune disease. When two or more moesin fragments representing different moesin domains are used in the antibody detection panel (such as an ELISA assay), the methods can further comprising comparing relative autoantibody levels for different moesin fragments and correlating the differences with disease type, disease stage or treatment response of the subject patient.

BRIEF DESCRIPTION OF THE DRAWINGS

FIG. 1. Amino acid sequence of the full length human moesin protein (SEQ ID NO:1, also referred as to Moesin-5).

FIG. 2. Amino acid sequence of moesin fragments: Moesin-1 (SEQ ID NO:2); Moesin-2 (SEQ ID NO:3); Moesin-3 (SEQ ID NO:4); Moesin-4 (SEQ ID NO:5).

FIG. 3. cDNA sequence encoding for the full length human moesin protein (SEQ ID NO:6).

MODES FOR CARRYING OUT THE INVENTION

Figure 4:
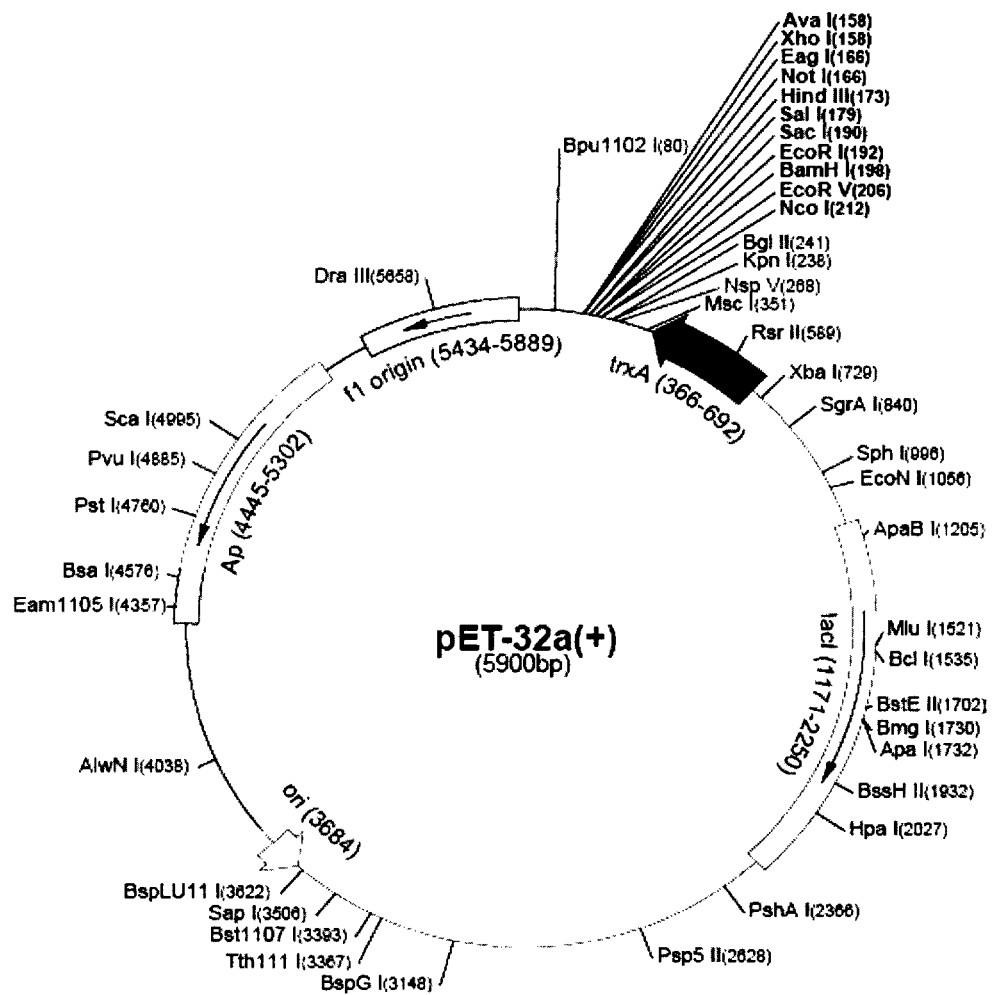
FIG. 4. Cloning map of the pET32a(+) expression vector.

The practice of the present application will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" series (Academic Press, Inc.); "Current Protocols in Molecular Biology" (F. M. Ausubel et al., eds., 1987, and periodic updates); "PCR: The Polymerase Chain Reaction", (Mullis et al., eds., 1994). Primers, polynucleotides and polypeptides employed in the present application can be generated using standard techniques known in the art.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

Definitions

The term "moesin" stands for membrane-organizing extension spike protein, as described in Lankes and Furthmayr (1991) Proc. Natl. Acad. Sci., 88:8297-8301. Full length human moesin protein is a 577-amino acid polypeptide having an amino acid sequence as set forth in FIG. 1 (SEQ ID NO:1). The moesin protein consists of three domains: the N-terminal FERM domain, the helical domain, and the C-terminal tail domain, as further defined below. It belongs to the ERM (ezrin-radixin-moesin) family. The three ERM proteins, primarily expressed in cytoplasm right beneath the plasma membrane, share high degrees of sequence homology and act as linking proteins between the plasma membrane and the actin cytoskeleton. Furthermore, human moesin protein shares high degrees of sequence homology with moesins from other species such as mouse and bovine moesins. Sato et al. (1992) J. Cell Sci. 103:131-143.

The term "moesin fragment" refers to a portion of the moesin polypeptide that is shorter than the full length wild type moesin protein, and that is capable of binding to an anti-moesin autoantibody. Useful in the present application are such moesin fragments capable of binding to domain-specific anti-moesin autoantibodies. A "fragment" of the moesin fragment means a portion of the moesin fragment that is shorter than such moesin fragment, and that retains the ability of binding to an anti-moesin autoantibody.

The "N-terminal FERM domain" of human moesin protein refers to the globular portion of the wild type human moesin protein structurally proximate to the amino-terminal of the protein and functionally responsible for localizing the protein to the plasma membrane and interacting with adhesion molecules. The FERM domain, which stands for band four-point-one, ezrin, radixin, moesin homology domain because of its homology with the band 4.1 protein, defines members of the band 4.1 superfamily, which includes cytoskeletal proteins such as erythrocyte band 4.1, talin, and the ezrin-radixin-moesin (ERM) protein family, as well as several tyrosine kinases and phosphatases and the tumor suppressor protein merlin. Specifically, the term refers to the first about 297 amino acid residues of the mature form of human moesin protein (e.g., amino acid residues 1-297 (SEQ ID NO:2)). In certain literatures, the same domain is also known as N-ERM associated domain (N-ERMAD), which is included in the definition herein. Bretscher et al. (1995) Biochem. 34, 16830-7.

The "C-terminal tail domain" of human moesin protein refers to the portion of the wild type human moesin protein structurally proximate to the carboxy-terminal of the protein and functionally responsible for binding to and interacting with actin filaments. The tail domain of moesin is positively charged and adopts an extended, meandering structure. Specifically, the term refers to the last about 107 amino acid residues of human moesin protein (e.g., amino acid residues 471-577 (SEQ ID NO:5)). In certain literatures, the same domain is also known as C-ERM associated domain (C-ERMAD), which is included in the definition herein. Bretscher et al. (1995). The last 34 amino acid residues of the C-terminal tail domain are highly conserved amongst ERM proteins and forms the region for binding to F-actin. Within the F-actin binding region, there exists a threonine residue (Thr558 in wild type human moesin) that is phosphorylated during the activation of the protein.

The "helical domain" of human moesin protein refers to the central portion of the wild type human moesin resided in between the N-terminal FERM domain and the C-terminal tail domain. It adopts an extended alpha-helical structure, acting as a linker between the two terminal domains. Specifically the term refers to the region encompassing about amino acid residues 298-470 of human moesin protein (SEQ ID NO:4).

The term "anti-moesin autoantibody" refers to an anti-moesin antibody produced by an individual's immune system that recognizes and binds to such individual's own moesin protein or fragments thereof. The presence of anti-moesin autoantibody can be associated with an autoimmune disorder, and the titer of such anti-moesin autoantibody in the body may correlate to the pathological state of the autoimmune disorder.

The term "diagnosis" is used herein to refer to the identification of a molecular or pathological state, disease or condition, such as the identification of an autoimmune disease, or to refer to identification of a patient with autoimmune disease who may benefit from a particular treatment regimen. In one embodiment, diagnosis refers to the identification of a particular type of autoimmune disorder. In yet another embodiment, diagnosis refers to the identification of autoimmune disorder associated with higher than normal presence of anti-moesin autoantibodies in a subject.

The term "prognosis" is used herein to refer to the prediction of the likelihood of outcomes of disease symptoms, including, for example, recurrence, flaring, and drug resistance, of a disease. The term also refers to the prediction of the likelihood of clinical benefit from a therapy.

The term "prediction" is used herein to refer to the likelihood that a patient will respond either favorably or unfavorably to a drug or set of drugs or a particular therapy course. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the present application can be used clinically to make treatment decisions by choosing the most appropriate treatment modalities for any particular patient. The predictive methods of the present application are valuable tools in predicting if a patient is likely to respond favorably to a treatment regimen, such as a given therapeutic regimen, including for example, administration of a given therapeutic agent or combination, surgical intervention, steroid treatment, etc., or whether long-term survival of the patient, following a therapeutic regimen is likely.

An "autoimmune disorder" or "autoimmune disease" herein is a disease or disorder arising from an immune response directed against an individual's own substances and tissues. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE) (including but not limited to lupus nephritis, cutaneous lupus); diabetes mellitus (e.g. Type I diabetes mellitus or insulin dependent diabetes mellitis); multiple sclerosis; Reynaud's syndrome; autoimmune thyroiditis; Hashimoto's thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (YIP) or autoimmune thrombocytopenia etc.

"Sample" or "test sample" herein refers to a composition that is obtained or derived from a subject of interest that contains a cellular and/or other molecular entity that is to be characterized and/or identified, for example based on physical, biochemical, chemical and/or physiological characteristics. In one embodiment, the definition encompasses blood and other liquid samples of biological origin and tissue samples such as a biopsy specimen or tissue cultures or cells derived therefrom or cell culture. The source of the tissue sample may be solid tissue as from a fresh, frozen and/or preserved organ or tissue sample or biopsy or aspirate; blood or any blood constituents such as plasma or serum; bodily fluids; and cells from any time in gestation or development of the subject or plasma. In another embodiment, the sample is whole blood, serum or plasma obtained from a subject. A subject can be a human or an animal subject. In another embodiment, a subject has or is suspected of having an autoimmune disorder. In another embodiment, the definition includes biological samples that have been manipulated in any way after their procurement, such as by treatment with reagents, solubilization, or enrichment for certain components, such as proteins or polynucleotides.

In one embodiment, a sample is obtained from a subject or patient prior to any treatment. In another embodiment, a test sample is obtained during or after treatment such as autoimmune disorder therapy. In one embodiment, the test sample is a clinical sample. In another embodiment, the test sample is used in a diagnostic assay. In another embodiment, the sample is pre-tested with other known clinical techniques before being tested with the methods of the present application. In certain embodiments, the sample is pre-tested for, for example, full blood count, liver enzymes, renal function, vitamin $B_{12}$ levels, folic acid levels, erythrocyte sedimentation rate, peripheral blood smear, bone marrow biopsy and the like.

A "reference sample", "reference cell", or "reference tissue", as used herein, refers to a sample, cell or tissue obtained from a source known, or believed, not to be afflicted with the disease or condition for which a method or composition of the present application is being used to identify. In one embodiment, a reference sample, reference cell or reference tissue is obtained from a healthy part of the body of the same subject or patient in whom a disease or condition is being identified using a composition or method of the present application. In one embodiment, a reference sample, reference cell or reference tissue is obtained from a healthy part of the body of an individual who is not the subject or patient in whom a disease or condition is being identified using a composition or method of the present application.

A "reference database", as used herein, refers to a collection of data, standard, or level from one or more reference samples or disease reference samples. In one embodiment, such collection of data, standard or level are normalized so that they can be used for comparison purpose with data from one or more sample. "Normalize" or "normalization" is a process by which a measurement raw data is converted into data that may be directly compared with other so normalized data. Normalization is used to overcome assay-specific errors caused by factors that may vary from one assay to another, for example, variation in loaded quantities, binding efficiency, detection sensitivity, and other various errors. In one embodiment, a reference database includes titers of anti-moesin autoantibodies, platelet counts, blood cell counts, and/or other laboratory and clinical data from one or more reference samples or disease reference samples. In one embodiment, a reference database includes levels of anti-moesin autoantibodies that are each normalized as a percent of the level of anti-moesin autoantibody of a control sample (e.g. a known amount of anti-moesin autoantibody) tested under the same conditions as the reference samples or disease reference samples. In order to compare with such normalized levels of anti-moesin autoantibodies, the level of anti-moesin autoantibody of a test sample is also measured and calculated as a percent of the level of anti-moesin autoantibody of a control sample tested under the same conditions as the test sample. In one embodiment, a reference database is established by compiling reference sample data from healthy subjects and/or non-diseased part of the body of the same subject or patient in whom a disease or condition is being identified using a composition or method of the present application. In one embodiment, a reference database is established by compiling data from disease reference samples from individuals under treatment for autoimmune disease. In one embodiment, a reference database is established by compiling data from disease reference samples from individuals at different stages of autoimmune disease as evidenced by, for example, different levels of platelet counts and other clinical indications.

In certain embodiments, the term "increase" refers to an overall increase of 5%, 10%, 15%, 20%, 25%, 30%, 40%, 50%, 60%, 70%, 80%, 85%, 90%, 95%, 96%, 97%, 98%, 99% or greater, in the level of autoantibody, detected by standard art known methods such as those described herein, as compared to a reference sample or a disease reference sample. In certain embodiments, the term increase refers to the increase in the level of autoantibody in the sample wherein the increase is at least about 1.25×, 1.5×, 1.75×, 2×, 3×, 4×, 5×, 6×, 7×, 8×, 9×, 10×, 25×, 50×, 75×, or 100× the level of autoantibody in the reference sample.

In certain embodiments, the term "decrease" herein refers to an overall reduction of 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or greater, in the level of autoantibody, detected by standard art known methods such as those described herein, as compared to a reference sample or a disease reference sample. In certain embodiments, the term decrease refers to the decrease in the level of autoantibody in the sample wherein the decrease is at least about 0.9×, 0.8×, 0.7×, 0.6×, 0.5×, 0.4×, 0.3×, 0.2×, 0.1×, 0.05×, or 0.01× the level of the autoantibody in the reference sample.

The term "detection antibody" refers to an antibody that is capable of being detected either directly through a label amplified by a detection means, or indirectly through, e.g., another antibody that is labeled. For direct labeling, the antibody is typically conjugated to a moiety that is detectable by some means. In one embodiment, the detectable antibody is biotinylated antibody.

The term "detection means" refers to a moiety or technique used to detect the presence of the detectable antibody in the ELISA herein and includes detection agents that amplify the immobilized label such as label captured onto a microtiter plate. In one embodiment, the detection means is a colorimetric detection agent such as avidin or streptavidin-HRP. In another embodiment, the detection means is a $H_2O_2$/TMB coloring system.

The term "capture reagent" refers to a reagent capable of binding and capturing a target molecule in a sample such that under suitable condition, the capture reagent-target molecule complex can be separated from the rest of the sample. Typically, the capture reagent is immobilized or immobilizable. In a sandwich immunoassay, the capture reagent is preferably an antibody or a mixture of different antibodies against a target antigen.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of autoantibody detection, one may use the results of the detection analysis or protocol to determine whether a specific therapeutic regimen should be performed.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

An "isolated" polypeptide is one that has been identified and separated and/or recovered from contaminant components of its natural environment. Contaminant components of its natural environment are materials that would interfere with diagnostic or therapeutic uses for the polypeptide, and may include enzymes, hormones, and other proteinaceous or nonproteinaceous solutes. In certain embodiments, the polypeptide will be purified (1) to greater than 95% by weight of polypeptide as determined by the Lowry method, or more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue, or silver stain. Isolated polypeptide includes the polypeptide in situ within recombinant cells since at least one contaminant component of the polypeptide's natural environment will not be present. Ordinarily, however, isolated polypeptide will be prepared by at least one purification step.

The term "percent (%) amino acid sequence identify" with respect to a moesin domain or fragment of the present application is defined as the percentage of amino acid residues in a sequence of interest that are identical with the amino acid residues in the moesin domain or fragment, after aligning the sequences and introducing gaps, if necessary, to achieve the maximum percent sequence identity, and not considering any conservative amino acid substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. See, for example, Altschul et al., Nucleic Acids Res. 25:3389-3402 (1997); Altschul et al., Methods in Enzymology 266:460-480 (1996). Those skilled in the art can determine appropriate parameters for measuring alignment, including any algorithms needed to achieve maximal alignment over the full length of the sequences being compared.

The term "antibody" is used in the broadest sense and specifically covers monoclonal antibodies (including full length or intact monoclonal antibodies), polyclonal antibodies, multivalent antibodies, multispecific antibodies (e.g., bispecific antibodies) formed from at least two intact antibodies, and antibody fragments so long as they exhibit the desired antigen binding activity.

"Treatment" refers to both therapeutic treatment and prophylactic or preventative measures. Those in need of treatment include those already with the disorder as well as those in which the disorder is to be prevented.

Responsiveness of a patient can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesion size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) relief, to some extent, of one or more symptoms associated with the disorder; (7)

increase in the length of disease-free presentation following treatment; (8) decrease of auto-immune response, which may, but does not have to, result in the regression or ablation of the disease lesion, e.g., progression-free survival; (9) increased overall survival; (10) higher response rate; and/or (11) decreased mortality at a given point of time following treatment.

The term "benefit" is used in the broadest sense and refers to any desirable effect and specifically includes clinical benefit.

Typical Methods and Materials of the Invention

The present application provides compositions and methods for diagnosing and monitoring autoimmune disorders associated with the presence and titer of anti-moesin autoantibodies. Conventional methods known to the skilled in the art can be used to carry out the present application.

Vectors, Host Cells and Recombinant Methods

The polypeptides of the present application can be produced recombinantly, using techniques and materials readily obtainable. For recombinant production of a polypeptide of the present application, e.g., a protein of the present application, an antibody of a protein of the present application, the nucleic acid encoding it is isolated and inserted into a replicable vector for further cloning (amplification of the DNA) or for expression. DNA encoding the polypeptide of the present application is readily isolated and sequenced using conventional procedures. For example, a DNA encoding a human moesin protein is isolated and sequenced, e.g., by using oligonucleotide probes that are capable of binding specifically to genes encoding the protein. Many vectors are available. The vector components generally include, but are not limited to, one or more of the following: a signal sequence, an origin of replication, one or more selection genes, an enhancer element, a promoter, and a transcription termination sequence.

Signal Sequence Component

Polypeptides of the present application may be produced recombinantly not only directly, but also as a fusion polypeptide with a heterologous polypeptide, which is typically a signal sequence or other polypeptide having a specific cleavage site at the N-terminus of the mature protein or polypeptide. The heterologous signal sequence selected typically is one that is recognized and processed (i.e., cleaved by a signal peptidase) by the host cell. For prokaryotic host cells, the signal sequence can be a prokaryotic signal sequence selected, for example, from the group of the alkaline phosphatase, penicillinase, 1 pp, or heat-stable enterotoxin II leaders. For yeast secretion the native signal sequence may be, e.g., the yeast invertase leader, α factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the polypeptide of the present application.

Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid, such as DHFR, thymidine kinase, metallothionein-I and -II, typically primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding a polypeptide of the present application, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid Yrp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

Promoter Component

Expression and cloning vectors usually contain a promoter that is recognized by the host organism and is operably linked to a nucleic acid encoding a polypeptide of the present application. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the polypeptide of the present application.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldyhyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription of polypeptides of the present application from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the rous sarcoma virus long terminal repeat can be used as the promoter.

Enhancer Element Component

Transcription of a DNA encoding a polypeptide of this invention by higher eukaryotes is often increased by inserting an enhancer sequence into the vector. Many enhancer sequences are now known from mammalian genes (globin, elastase, albumin, α-fetoprotein, and insulin). Typically, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the polypeptide-encoding sequence, but is typically located at a site 5' from the promoter.

Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide of the present application. One useful transcription termination component is the bovine growth hormone polyadenylation region. See WO94/11026 and the expression vector disclosed therein.

Selection and Transformation of Host Cells

Suitable host cells for cloning or expressing DNA encoding the polypeptides of the present application in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. Typically, the *E. coli* cloning host is *E. coli* 294 (ATCC 31,446), although other strains such as *E. coli* B, *E. coli* BL21(DE3), *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for vectors encoding for polypeptide of the present application-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of polypeptides of the present application can be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present application, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for production of polypeptide of the present application and cultured in conventional nutrient media modified as appropriate for inducing promoters, selecting transformants, or amplifying the genes encoding the desired sequences.

Culturing the Host Cells

The host cells used to produce polypeptides of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Chemical Synthesis of Peptides

The peptides of the present application can also be produced by chemical synthesis, for example, the solid phase synthesis method described by Merrifield in J.A.C.S. 85: 2149-2154 (1963) and the variations thereof, or otherwise the standard solution synthesis method described in "Peptide Synthesis" by Bodanszky, et al, second edition, John Wiley and Sons, 1976 and the variations thereof. These publications are entirely incorporated herein by reference.

Briefly, synthesis of a peptide by using solid phase synthesis method involves initially attaching the protected C-terminal amino acid of the peptide to the resin. After attachment the resin is filtered, washed and the protecting group (e.g. t-butyloxycarbonyl) on the alpha amino group of the C-terminal amino acid is removed. The removal of this protecting group must take place, of course, without breaking the bond between that amino acid and the resin. To the resulting resin peptide is then coupled the penultimate C-terminal protected amino acid. This coupling takes place by the formation of an amide bond between the free carboxy group of the second amino acid and the amino group of the first amino acid attached to the resin. This sequence of events is repeated with successive amino acids until all amino acids of the peptide are attached to the resin. Finally, the protected peptide is cleaved from the resin and the protecting groups removed to obtain the desired peptide. The cleavage techniques used to separate the peptide from the resin and to remove the protecting groups depend upon the selection of resin and protecting groups and are known to those familiar with the art of peptide synthesis.

The resin mentioned above may be any suitable polymer and shall contain a functional group to which the first protected amino acid can be firmly linked by a covalent bond. Various polymers are suitable for this purpose, such as cellulose, polyvinyl alcohol, polymethylmethacrylate, and polystyrene. Appropriate protecting groups usable in solid phase synthesis include t-butyloxycarbonyl (BOC), benzyl (BZL), t-amyloxycarbonyl (AOC), tosyl (TOS), o-bromophenylmethoxycarbonyl (BrZ),2,6-dichlorobenzyl (BZLC1.sub.2), and phenylmethoxycarbonyl (Z or CBZ). Additional protecting groups are also described in J. F. W. McOmie, "Protective Groups in Organic Chemistry", Plenum Press, New York, 1973. This book is entirely incorporated herein by reference.

The standard solution synthesis method can be performed by either stepwise or block coupling of amino acids or peptide fragments using chemical or enzymatic methods of amide bond formation. These solution synthesis methods are well known in the art.

Polypeptide Purification

A polypeptide or protein of the present application may be recovered from a subject. When using recombinant techniques, a polypeptide of the present application can be produced intracellularly, in the periplasmic space, or directly secreted into the medium. Polypeptides of the present application may be recovered from culture medium or from host cell lysates. If membrane-bound, it can be released from the membrane using a suitable detergent solution (e.g. Triton-X 100) or by enzymatic cleavage. Cells employed in expression of a polypeptide of the present application can be disrupted by various physical or chemical means, such as freeze-thaw cycling, sonication, mechanical disruption, or cell lysing agents.

If a peptide is chemically synthesized, the peptide of the present application may be recovered from the reaction medium by any suitable techniques capable of separating peptide of interest from other components in the medium. For a solid phase synthesis, the protected peptide is firstly cleaved off the resin using a suitable cleaving solution. The selection of cleaving solution depends upon the properties of the resin and the amino acid bound thereto (such as trifluoroacetic acid for FMOC method). Cleaving is usually carried out under acid condition. Upon completion of cleaving, a dissociative peptide is then obtained and further purified using any suitable techniques (such as the methods described below).

The following procedures are exemplary of suitable protein purification procedures: by fractionation on an ion-exchange column; ethanol precipitation; reverse phase HPLC; chromatography on silica, chromatography on heparin SEPHAROSE™ chromatography on an anion or cation exchange resin (such as a polyaspartic acid column, DEAE, etc.); chromatofocusing; SDS-PAGE; ammonium sulfate precipitation; gel filtration using, for example, SEPHADEX G-75; protein A SEPHAROSE columns to remove contaminants such as IgG; and metal chelating columns to bind epitope-tagged forms of polypeptides of the present application. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular polypeptide of the present application produced.

Detection Methods

In the methods of the present application, a biological sample is obtained from a subject suspected of having autoimmune disorder and examined for expression of one or more anti-moesin autoantibodies. Expression of various anti-moesin autoantibodies in a sample can be analyzed by a number of methodologies, many of which are known in the art and understood by the skilled artisan, including but not limited to, enzyme-linked immunosorbent assay (ELISA), enzyme-linked immuno-flow assay (ELIFA), immunoblotting, Western blot analysis, immunohistochemical analysis, immunoprecipitation, molecular binding assays and the like. Multiplexed immunoassays such as those available from Rules Based Medicine or Meso Scale Discovery (MSD) may also be used. These methods include both single-site and two-site or "sandwich" assays of the non-competitive types, as well as in the traditional competitive binding assays. Detection can be conducted in vitro, in vivo or ex vivo.

Sandwich assays are among the most useful and commonly used assays. A number of variations of the sandwich assay technique exist, and all are intended to be encompassed by the present application. Briefly, in a typical forward sandwich assay, an unlabelled capture reagent (e.g., a moesin fragment) is immobilized on a solid substrate, and the sample to be tested for the target protein (e.g., an anti-moesin autoantibody) is brought into contact with the bound molecule. After a suitable period of incubation, for a period of time sufficient to allow formation of an antibody-antigen complex, a detection antibody specific to the target protein (e.g. through binding to the Fc region of the anti-moesin autoantibody), labelled with a reporter molecule capable of producing a detectable signal is then added and incubated, allowing time sufficient for the formation of another complex of capture reagent-target protein-detection antibody. Any unreacted material is washed away, and the presence of the target protein is determined by observation of a signal produced by the reporter molecule. The results may either be qualitative, by simple observation of the visible signal, or may be quantitated by comparing with a control sample containing known amounts of the reporter molecule.

In a typical forward sandwich assay, a capture reagent having specificity for the target protein is either covalently or passively bound to a solid support. The solid support is typically glass or a polymer, the most commonly used polymers being cellulose, polyacrylamide, nylon, polystyrene, polyvinyl chloride or polypropylene. The solid supports may be in the form of tubes, beads, discs of microplates, or any other support suitable for conducting an immunoassay.

Variations on the forward assay include a simultaneous assay, in which both sample and detection antibody are added simultaneously to the capture reagent. These techniques are well known to those skilled in the art, including any minor variations as will be readily apparent. Another alternative method involves immobilizing the target protein in the sample and then exposing the immobilized target proteins to the peptides of the present application which may or may not be labeled with a reporter molecule. Depending on the amount of target protein and the strength of the reporter molecule signal, a bound target protein may be detectable by direct labeling with the capture reagent (e.g. moesin fragment). Alternatively, a second detection antibody, specific to the capture reagent is exposed to the target protein-capture reagent complex to form a target protein-capture reagent-detection antibody tertiary complex. The complex is detected by the signal emitted by the reporter molecule.

The term "reporter molecule", as used herein, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In certain embodiments, the reporter molecules are enzymes conjugated to the detection antibodies. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. When activated by illumination with light of a particular wavelength, the fluorochrome adsorbs the light energy, inducing a state to excitability in the molecule, followed by emission of the light at a characteristic color visually detectable with a light microscope. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et ah, Methods for the Preparation of Enzyme-Antibody Conjugates for use in Enzyme Immunoassay, in Methods in Enzym. (ed. J. Langone & H. Van Vunakis), Academic press, New York, 73:147-166 (1981).

Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-(β-D-galactosidase) or fluorogenic substrate (e.g., 4-methylumbelliferyl-(β-D-galactosidase). Numerous other enzyme-substrate combinations are available to those skilled in the art. For a general review of these, see U.S. Pat. Nos. 4,275,149 and 4,318,980.

In certain embodiments, the reporter molecules are fluorophores including, but are not limited to, rare earth chelates (europium chelates), TEXAS RED, rhodamine, fluorescein, dansyl, LISSAMINE, umbelliferone, phycocrytherin, phycocyanin, or commercially available fluorophores such SPECTRUM ORANGE7 and SPECTRUM GREEN7 and/or derivatives of any one or more of the above. The fluorophores can be conjugated to the antibody using the techniques disclosed in Current Protocols in Immunology, Volumes 1 and 2, Coligen et al, Ed. Wiley-Interscience, New York, Pubs. (1991), for example. Fluorescence can be quantified using a fluorimeter.

In certain embodiments, the report molecules are radio-isotopes, such as $^{35}S$, $^{14}C$, $^{125}I$, $^{3}H$, and $^{131}I$. The detection antibody or capture reagent can be labeled with the radio-isotope using the techniques described in Current Protocols in Immunology, supra, for example and radioactivity can be measured using scintillation counting.

Sometimes, the label is indirectly conjugated with the detection antibody or capture reagent. The skilled artisan will be aware of various techniques for achieving this. For example, the detection antibody can be conjugated with biotin and the label can be conjugated with avidin, or vice versa. Biotin binds selectively to avidin and thus, the label can be conjugated with the detection antibody in this indirect manner. Alternatively, to achieve indirect conjugation of the label with the detection antibody, the detection antibody is conjugated with a small hapten and the label is conjugated with an anti-hapten antibody. Thus, indirect conjugation of the label with the antibody can be achieved.

In certain embodiments, the detection method is a competitive binding assay in which a competing anti-moesin antibody is used. Such competing antibody is capable of competing with moesin auto-antibodies for binding to the peptides of the present application. In a competitive binding assay, the reduction of binding signals can be indicative of the existence and titer of the corresponding auto-antibodies.

Diagnostic Kits

For use in the applications described or suggested above, kits or articles of manufacture are also provided by the present application. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be a moesin fragment specific for anti-moesin autoantibody.

The kits of the present application will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

The kits of the present application have a number of embodiments. A typical embodiment is a kit comprising a container, a label on said container, and a composition contained within said container; wherein the composition includes a peptide of the present application that can bind to an anti-moesin autoantibody, the label on said container indicates that the composition can be used to evaluate the presence of anti-moesin autoantibodies in a sample, and instructions for using the peptide of the present application for evaluating the presence of anti-moesin autoantibodies in a sample. The kit can further comprise a set of instructions and materials for preparing a tissue sample and applying the peptide of the present application to the sample. The kit may include a secondary antibody, wherein the secondary antibody is conjugated to a label, e.g., an enzymatic label.

Other optional components in the kit include one or more buffers (e.g., block buffer, wash buffer, substrate buffer, etc), other reagents such as substrate (e.g., chromogen) which is chemically altered by an enzymatic label, epitope retrieval solution, control samples (positive and/or negative controls), control slide(s) etc.

The following are examples of the methods and compositions of the present application. It is understood that various other embodiments may be practiced, given the general description provided above.

EXAMPLES

Example 1

Generation of Moesin Fragment Series

The following five moesin fragments are produced:
a. Moesin-1, containing amino acids 1-297 of human moesin protein (SEQ ID NO:2), near N-terminal domain of the human moesin protein;
b. Moesin-2, containing amino acids 298-577 of human moesin protein (SEQ ID NO:3), near the helical and C-terminal tail domains of the human moesin protein;
c. Moesin-3, containing amino acids 298-470 of human moesin protein (SEQ ID NO:4), near the helical domain of the human moesin protein;
d. Moesin-4, containing amino acids 471-577 of human moesin protein (SEQ ID NO:5), near the C-terminal tail domain of the human moesin protein; and
e. Moesin-5: full length human moesin protein, amino acid 1-577 (SEQ ID NO:1).

The full length Moesin cDNA sequence (1-1743 bp) was obtained from Genebank (Accession No. M69066) and shown in FIG. 3. To generate the above moesin fragments, PCR was used to amplify cDNA fragments corresponding to different amino acid fragments as described above.

Figure 5:
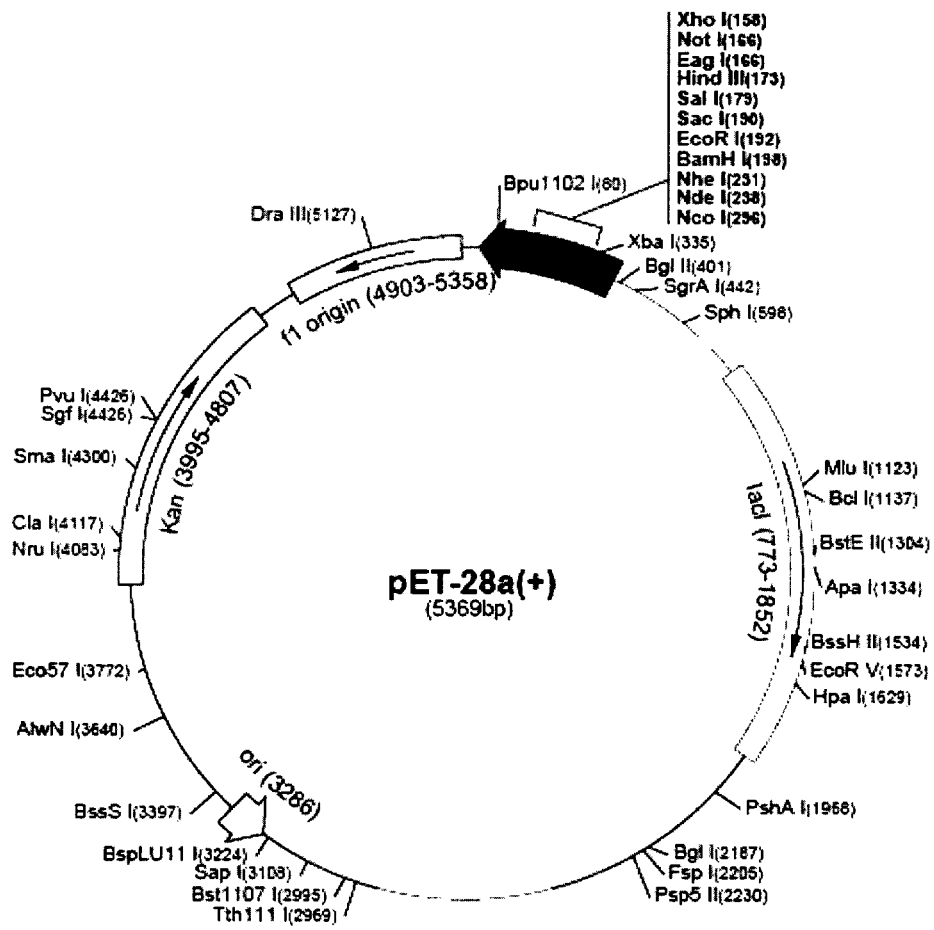
FIG. 5. Cloning map of the pET28a(+) expression vector.

PCR-amplified moesin DNA fragments were cloned into expression vectors selected from pET32a(+) and pET28a(+). The constructed vectors were then used to transform *E. coli* host cell line BL21(DE3) for culturing and expression. The restriction and cloning maps of pET32a(+) and pET28a(+) are shown in FIGS. 4 and 5, respectively. The constructed expression systems for various moesin fragments were verified with restriction enzyme digestion followed by sequencing to confirm the correct reading frame for expression of moesin fragments.

After sufficient culturing, host cells with expressed moesin fragments were harvested for collection and purification of moesin fragments according to standard protein expression protocols. The resulting protein fragments were assayed with SDS-PAGE to confirm their identity and purity.

Example 2

Detection and Measurement of Specific Anti-Moesin Autoantibodies in Sera of Patients with Autoimmune Disorders Sera or plasma samples were collected from patients with various stages of autoimmune diseases and tested for the presence of anti-moesin autoantibodies that recognize and bind to specific regions of the moesin protein. Patients' profiles and clinical information were used to categorize them based on types and stages of their diseases.

Moesin fragments obtained from Example 1 were used as antigens in ELISA assays for anti-moesin antibodies. Specifically, each micro well of the ELISA plate was coated with about 400 ng of moesin fragment at 2° C. to 8° C. for 12-16 hours, and then washed with PBS once before being blocked with blocking solution and vacuum dried for storage and later use. So a highly purified moesin fragment antigen was bound to the wells of a polystyrene microwell plate under conditions that would preserve the antigen in its native state.

Sera samples were collected and prepared from 6 different patient groups and 3 control groups for later ELISA testing. The patients in the patient groups all suffered from immune disorders, including 300 patients that were clinically diagnosed with CTD, 50 patients that were clinically diagnosed with Systemic Sclerosis, 70 patients that were clinically diagnosed with PAH, 300 patients that were clinically diagnosed with Sjogren's Syndrome, 80 patients that were clinically diagnosed with Rheumatoid Arthritis, and 45 patients that were clinically diagnosed with acquired aplastic anemia. The 3 control groups in which the individuals were either healthy or suffered from a non-immune disease included 83 patients that were clinically diagnosed with lung diseases (Control-1), 65 patients that were clinically diagnosed as tumor (Control-2), and 150 healthy donors (Control-3).

The controls and patient sera were diluted using PBS-T buffer (i.e. PBS buffer containing 0.05% (v/v) of TWEEN-20), and 100 µl of such diluted controls and diluted patient sera were then added to each well, allowing any anti-moesin antibodies present to bind to the immobilized antigen. Unbound sample was washed away using PBS-T buffer and an enzyme labeled anti-human IgG conjugate was added to each well. A second incubation allowed the enzyme labeled anti-human IgG to bind to any anti-moesin antibodies which have become attached to the micro wells. After washing away any unbound enzyme labeled anti-human IgG, the remaining enzyme activity was measured by adding a chromogenic substrate($H_2O_2$/TMB) and measuring the intensity of the color that develops. 100 µl of HRP Stop Solution (e.g., 2M $H_2SO_4$) were then added to each well. Sequence and timing of adding and maintaining HRP Stop Solution were according to TMB Chromogen. Each ELISA plate was gently tapped with fingers to thoroughly mix the wells.

The assay was evaluated using a spectrophotometer to measure and compare the color intensity that developed in the patient wells with the color in the control wells. Specifically, bichromatic measurements are used to measure and compare the color intensity, wherein both $OD_{450}$ value and $OD_{630}$ value (as a reference) of each well were read within 15 mins of stopping the reaction. The OD value of each test or control sample was calculated by subtracting the $OD_{450}$ value with the $OD_{630}$ value.

The ELISA low positive control, the ELISA high positive control and the ELISA negative control were run with every batch of samples to ensure that all reagents and procedures performed properly. The ELISA negative control was sera collected from healthy individuals. The OD values of sera collected from 50 healthy individuals were each measured and the average OD value (the "Control OD Value") and the standard deviation (the "Control Standard Deviation") from those 50 samples were calculated. Such Control OD Value and Control Standard Deviation were used to determine the concentrations of the ELISA low positive control and high positive control. The ELISA low positive control contains sera from patients with immune thrombocytopenia that were diluted enough to show an OD value which equals to the Control OD Value plus three times of the Control Standard Deviation. The ELISA high positive control contains sera from patients with immune thrombocytopenia that was diluted to show an OD value which equals to three times of the OD value of the ELISA low positive control. The dilution was done using 0.01M PBS-T buffer.

The average OD value for each set of duplicates of a sample was first determined and used as the titer of the sample, and the sample was determined positive if its average OD value was higher than the average OD value of the ELISA low positive control (as shown in Table 1).

As the skilled artisan will appreciate, the step of correlating a marker level to the presence or absence of specified diseases can be performed and achieved in different ways. In general a reference population is selected and a normal range established. It is fairly routine to establish the normal range for anti-moesin antibodies using an appropriate reference population. It is generally accepted that the normal range depends, to a certain but limited extent, on the reference population in which it is established. In one aspect, the reference population is high in number, e.g., hundreds to thousands, and matched for age, gender and optionally other variables of interest. The normal range in terms of absolute values, like a concentration given, also depends on the assay employed and the standardization used in producing the assay.

The levels for anti-moesin antibodies can be measured and established with the assay procedures given in the examples section. It has to be understood that different assays may lead to different cut-off values.

The clinical performance of a laboratory test depends on its diagnostic accuracy, or the ability to correctly classify subjects into clinically relevant subgroups. Diagnostic accuracy measures the test's ability to correctly distinguish different conditions of the subjects investigated. Such conditions are for example health and disease or benign versus malignant disease. That is, a significant higher value obtained from certain patient population indicates the positive presence of the corresponding anti-moesin autoantibody.

The results of the experiments are listed in the following table comparing various patient groups for the positive presences of different anti-moesin antibodies specific to certain moesin fragments (Table 1):

TABLE 1

Comparison of the Positive Presence of Anti-moesin Autoantibody to Specific
Moesin Fragments in Sera of Patient Groups and Control Group

| Patient Group | Number of Patients | Anti-Each Moesin Fragment positive | | | |
|---|---|---|---|---|---|
| | | Moesin 1 | Moesin 3 | Moesin 4 | Moesin 2 |
| Control-1 (lung diseases: including pneumonia, phthisis) | 83 | 5 (6.0%) | 14 (16.9%) | 10 (12.0%) | 11 (13.3%) |
| Control-2 (tumor: including lung cancer, breast cancer, colorectal carcinoma) | 65 | 1 (1.5%) | 0 (0) | 1 (1.5%) | 1 (1.5%) |
| Control-3 (healthy donors) | 150 | 2 (1.3%) | 3 (2.0%) | 4 (2.7%) | 3 (2.0%) |
| CTD | 300 | 122 (40.7%) | 41 (13.7%) | 39 (13.0%) | 45 (15.0%) |
| Systemic Sclerosis | 50 | 15 (30.0%) | 12 (24.0%) | 10 (20.0%) | 14 (28.0%) |
| PAH | 70 | 8 (11.4%) | 25 (35.7%) | 23 (32.9%) | 17 (24.3%) |
| Sjogren's Syndrome | 300 | 136 (45.3%) | 54 (18.0%) | 71 (23.7%) | 66 (22.0%) |
| Rheumatoid Arthritis | 80 | 3 (3.8%) | 7 (8.8%) | 6 (7.5%) | 10 (12.5%) |
| Acquired Aplastic Anemia) | 45 | 1 (2.2%) | 1 (2.2%) | 19 (42.2%) | 18 (40.0%) |

As shown in Table 1, the higher than normal presence (i.e. positive rate) of anti-moesin autoantibodies that specifically recognize and bind to the N-terminal FERM domain of moesin (Moesin-1) is significantly correlated with the incidence of CTD (about 41%). It indicates that that moesin fragments comprising amino acids of Moesin-1 can be used as diagnostic or prognostic markers for identifying patients having or suspected of having CTD.

Autoantibody titers for different moesin fragments were also measured in controls and different disease groups. Table 2 lists the mean titers and standard deviation of autoantibodies to specific moesin fragments in sera of Sjogren's syndrome patients.

TABLE 2

Titers of Autoantibody to Specific Moesin Fragments in Sera of
Sjogren's Syndrome Patients (300 Patients)

| | Moesin 1 | Moesin 3 | Moesin 4 | Moesin 2 | Moesin 5 |
|---|---|---|---|---|---|
| Mean Titer ($\bar{x}$) | 0.219133333 | 0.406857143 | 0.3160625 | 0.280133333 | 0.252886364 |
| STD | 0.050839587 | 0.178707796 | 0.148453121 | 0.114615423 | 0.10121982 |

As shown in Table 2, autoantibodies specific to the helical domain of moesin (Moesin-3) has the highest titer, followed closely by the C-terminal tail domain (Moesin-4). Statistic analysis of the data in Table 2 shows that the mean titers of the moesin fragments have significant statistical difference. See the results in Table 3.

TABLE 3

Statistic Significance of Difference between Autoantibody
Titers in Table 2
Mean Titer Value Comparison (t test)

| | Moesin-3 | Moesin-4 | Moesin-2 | Moesin-5 |
|---|---|---|---|---|
| Moesin-1 | significant | significant | significant | significant |
| Moesin-3 | / | significant | significant | significant |
| Moesin-4 | / | / | no difference | significant |
| Moesin-2 | / | / | / | no difference |

Therefore, moesin fragments comprising amino acids of either the helical or the tail domain, or both, of moesin can be used as diagnostic or prognostic markers for identifying patients having or suspected of having Sjogren's Syndrome.

Similar analysis of domain-specific autoantibodies in terms of their percentage of presence in patients and their levels have been conducted for other disease groups.

Example 3

Correlation of Autoantibody Levels with Disease Types and Disease States

The autoantibody data obtained from existing patients with autoimmune disease and various control groups are used individually as reference data points or collectively to establish reference databases. Theses reference data are then used to establish the correlation of presence/level of autoantibodies in a test sample with particular autoimmune disease and their disease states associated with the individual subject from whom the test sample is obtained. Detection and measurement of autoantibodies in the test sample is conducted using the ELISA assay as described above in Example 2.

In one experiment, the sera sample from an individual suspected of having an autoimmune disease is tested for presence and levels of autoantibodies specific to multiple moesin fragments representing different moesin domains. Specifically, a first set of micro wells of the ELISA plate are coated with moesin fragments derived from the N-terminal FERM domain; a second set of micro wells are coated with moesin fragments derived from the helical domain; and a third set of micro wells are coated with moesin fragments derived from the C-terminal tail domain. Once the moesin fragments are immobilized and stabilized to their separate wells, diluted patient sera are added to each well, under conditions allowing antibody-antigen binding. After a series of washing and labeling steps, each well is measured for $OD_{450}$ value to detect and quantify antibodies bound to the specific moesin fragment.

The $OD_{450}$ values from a set of wells that represent autoantibodies to a particular moesin domain are compiled and compared to the reference database or a reference sample data to determine the subject patient's disease status—whether he/she has a particular type of autoimmune disease and the stage of the disease. A matrix analysis of relative levels of autoantibodies to different moesin domains is also used to assist in determining the subject's disease status. If a patient has low level of autoantibodies to the N-terminal FERM domain but high level of autoantibodies to the helical or C-terminal tail domain, she is likely developing fibrosis related disorders such as the Sjogren's Syndrome or systemic sclerosis. If a patient has high level of autoantibodies to the C-terminal tail domain, either alone, or in combination with low levels of autoantibodies to the N-terminal FERM domain and the helical domain, he is likely developing pathological conditions associated with abnormal apoptosis of epithelial cells or endothelial cells such as aplastic anemia. Quantitatively, the relative fold differences in levels of autoantibodies to different moesin domains are also used to correlate with disease types and disease states.

What is claimed is:

1. A method of detecting an anti-moesin autoantibody in a subject suspected of having an autoimmune disorder, comprising the following steps:
   a) providing a composition comprising a moesin fragment consisting of SEQ ID NO:2,
   b) contacting under antigen-antibody binding conditions said moesin fragment with a sample obtained from said subject; and
   c) determining a level of the anti-moesin autoantibody in said sample;
   wherein the autoimmune disorder is selected from connective tissue disease (CTD), systemic sclerosis and Sjorgren's Syndrome.

2. The method of claim 1, further comprising the following step:
   d) comparing the level of the anti-moesin autoantibody in said sample from step c) to a reference database correlating anti-moesin autoantibody levels to pathological states of the autoimmune disorder.

3. The method of claim 1, wherein the subject is undergoing a treatment for the autoimmune disorder, further comprising the following step:
   d) comparing the level of the anti-moesin autoantibody in said sample from step c) to an anti-moesin autoantibody level in a reference sample obtained from the same subject prior to the treatment.

4. The method of claim 1, further comprising the following step:
   d) comparing the level of the anti-moesin autoantibody in said sample from step c) to an established normal range of anti-moesin autoantibody levels.

5. The method of claim 1, wherein the subject has pulmonary complications.

6. The method of claim 1, wherein the subject has one or more symptoms selected from the group consisting of pulmonary arterial hypertension (PAH), interstitial lung disease (ILD), lung fibrosis, chronic obstructive pulmonary disease, bronchiectasis and lung infection.

7. The method of claim 1, wherein the moesin fragment is conjugated to a carrier.

8. The method of claim 1, wherein the composition of step a) further comprises an additional separate moesin fragment consisting of SEQ ID NO:4.

9. The method of claim 1, wherein the composition of step a) further comprises an additional separate moesin fragment consisting of SEQ ID NO:5.

* * * * *

SEQUENCE LISTING

```
<160> NUMBER OF SEQ ID NOS: 6

<210> SEQ ID NO 1
<211> LENGTH: 577
<212> TYPE: PRT
<213> ORGANISM: Artificial
<220> FEATURE:
<223> OTHER INFORMATION: the Full Length Human Moesin Protein

<400> SEQUENCE: 1

Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Phe Phe Gly Leu Gln
        35                  40                  45

Tyr Gln Asp Thr Lys Gly Phe Ser Thr Trp Leu Lys Leu Asn Lys Lys
    50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Glu Leu Ile Gln Asp
                85                  90                  95

Ile Thr Gln Arg Leu Phe Phe Leu Gln Val Lys Glu Gly Ile Leu Asn
            100                 105                 110

Asp Asp Ile Tyr Cys Pro Pro Glu Thr Ala Val Leu Leu Ala Ser Tyr
        115                 120                 125

Ala Val Gln Ser Lys Tyr Gly Asp Phe Asn Lys Glu Val His Lys Ser
    130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175

Glu Glu His Arg Gly Met Leu Arg Glu Asp Ala Val Leu Glu Tyr Leu
            180                 185                 190

Lys Ile Ala Gln Asp Leu Glu Met Tyr Gly Val Asn Tyr Phe Ser Ile
        195                 200                 205

Lys Asn Lys Lys Gly Ser Glu Leu Trp Leu Gly Val Asp Ala Leu Gly
    210                 215                 220

Leu Asn Ile Tyr Glu Gln Asn Asp Arg Leu Thr Pro Lys Ile Gly Phe
225                 230                 235                 240
```

```
Pro Trp Ser Glu Ile Arg Asn Ile Ser Phe Asn Asp Lys Lys Phe Val
            245                 250                 255
Ile Lys Pro Ile Asp Lys Lys Ala Pro Asp Phe Val Phe Tyr Ala Pro
            260                 265                 270
Arg Leu Arg Ile Asn Lys Arg Ile Leu Ala Leu Cys Met Gly Asn His
            275                 280                 285
Glu Leu Tyr Met Arg Arg Lys Pro Asp Thr Ile Glu Val Gln Gln
            290                 295                 300
Met Lys Ala Gln Ala Arg Glu Glu Lys His Gln Lys Gln Met Glu Arg
305                 310                 315                 320
Ala Met Leu Glu Asn Glu Lys Lys Arg Glu Met Ala Glu Lys Glu
            325                 330                 335
Lys Glu Lys Ile Glu Arg Glu Lys Glu Glu Leu Met Glu Arg Leu Lys
            340                 345                 350
Gln Ile Glu Glu Gln Thr Lys Lys Ala Gln Gln Glu Leu Glu Glu Gln
            355                 360                 365
Thr Arg Arg Ala Leu Glu Leu Glu Gln Glu Arg Lys Arg Ala Gln Ser
            370                 375                 380
Glu Ala Glu Lys Leu Ala Lys Glu Arg Gln Glu Ala Glu Glu Ala Lys
385                 390                 395                 400
Glu Ala Leu Leu Gln Ala Ser Arg Asp Gln Lys Lys Thr Gln Glu Gln
            405                 410                 415
Leu Ala Leu Glu Met Ala Glu Leu Thr Ala Arg Ile Ser Gln Leu Glu
            420                 425                 430
Met Ala Arg Gln Lys Lys Glu Ser Glu Ala Val Glu Trp Gln Gln Lys
            435                 440                 445
Ala Gln Met Val Gln Glu Asp Leu Glu Lys Thr Arg Ala Glu Leu Lys
            450                 455                 460
Thr Ala Met Ser Thr Pro His Val Ala Glu Pro Ala Glu Asn Glu Gln
465                 470                 475                 480
Asp Glu Gln Asp Glu Asn Gly Ala Glu Ala Ser Ala Asp Leu Arg Ala
            485                 490                 495
Asp Ala Met Ala Lys Asp Arg Ser Glu Glu Arg Thr Thr Glu Ala
            500                 505                 510
Glu Lys Asn Glu Arg Val Gln Lys His Leu Lys Ala Leu Thr Ser Glu
            515                 520                 525
Leu Ala Asn Ala Arg Asp Glu Ser Lys Lys Thr Ala Asn Asp Met Ile
            530                 535                 540
His Ala Glu Asn Met Arg Leu Gly Arg Asp Lys Tyr Lys Thr Leu Arg
545                 550                 555                 560
Gln Ile Arg Gln Gly Asn Thr Lys Gln Arg Ile Asp Glu Phe Glu Ser
            565                 570                 575
Met

<210> SEQ ID NO 2
<211> LENGTH: 297
<212> TYPE: PRT
<213> ORGANISM: Artificial
<220> FEATURE:
<223> OTHER INFORMATION: N-terminal FERM domain of human moesin protein

<400> SEQUENCE: 2

Met Pro Lys Thr Ile Ser Val Arg Val Thr Thr Met Asp Ala Glu Leu
1               5                   10                  15
```

-continued

```
Glu Phe Ala Ile Gln Pro Asn Thr Thr Gly Lys Gln Leu Phe Asp Gln
             20                  25                  30

Val Val Lys Thr Ile Gly Leu Arg Glu Val Trp Phe Phe Gly Leu Gln
         35                  40                  45

Tyr Gln Asp Thr Lys Gly Phe Ser Thr Trp Leu Lys Leu Asn Lys Lys
 50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Glu Leu Ile Gln Asp
                 85                  90                  95

Ile Thr Gln Arg Leu Phe Phe Leu Gln Val Lys Glu Gly Ile Leu Asn
            100                 105                 110

Asp Asp Ile Tyr Cys Pro Pro Glu Thr Ala Val Leu Leu Ala Ser Tyr
        115                 120                 125

Ala Val Gln Ser Lys Tyr Gly Asp Phe Asn Lys Glu Val His Lys Ser
    130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175

Glu Glu His Arg Gly Met Leu Arg Glu Asp Ala Val Leu Glu Tyr Leu
            180                 185                 190

Lys Ile Ala Gln Asp Leu Glu Met Tyr Gly Val Asn Tyr Phe Ser Ile
        195                 200                 205

Lys Asn Lys Lys Gly Ser Glu Leu Trp Leu Gly Val Asp Ala Leu Gly
    210                 215                 220

Leu Asn Ile Tyr Glu Gln Asn Asp Arg Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Ala Leu Cys Met Gly Asn His
        275                 280                 285

Glu Leu Tyr Met Arg Arg Lys Pro
    290                 295

<210> SEQ ID NO 3
<211> LENGTH: 280
<212> TYPE: PRT
<213> ORGANISM: Artificial
<220> FEATURE:
<223> OTHER INFORMATION: helical and C-terminal tail domains of human
      moesin protein

<400> SEQUENCE: 3

Asp Thr Ile Glu Val Gln Gln Met Lys Ala Gln Ala Arg Glu Glu Lys
1               5                   10                  15

His Gln Lys Gln Met Glu Arg Ala Met Leu Glu Asn Glu Lys Lys Lys
            20                  25                  30

Arg Glu Met Ala Glu Lys Glu Lys Glu Ile Glu Arg Glu Lys Glu
        35                  40                  45

Glu Leu Met Glu Arg Leu Lys Gln Ile Glu Glu Gln Thr Lys Lys Ala
    50                  55                  60

Gln Gln Glu Leu Glu Glu Gln Thr Arg Arg Ala Leu Glu Leu Glu Gln
65                  70                  75                  80
```

-continued

```
Glu Arg Lys Arg Ala Gln Ser Glu Ala Glu Lys Leu Ala Lys Glu Arg
                85                  90                  95
Gln Glu Ala Glu Glu Ala Lys Glu Ala Leu Leu Gln Ala Ser Arg Asp
            100                 105                 110
Gln Lys Lys Thr Gln Glu Gln Leu Ala Leu Glu Met Ala Glu Leu Thr
        115                 120                 125
Ala Arg Ile Ser Gln Leu Glu Met Ala Arg Gln Lys Lys Glu Ser Glu
    130                 135                 140
Ala Val Glu Trp Gln Gln Lys Ala Gln Met Val Gln Glu Asp Leu Glu
145                 150                 155                 160
Lys Thr Arg Ala Glu Leu Lys Thr Ala Met Ser Thr Pro His Val Ala
                165                 170                 175
Glu Pro Ala Glu Asn Glu Gln Asp Glu Gln Asp Glu Asn Gly Ala Glu
            180                 185                 190
Ala Ser Ala Asp Leu Arg Ala Asp Ala Met Ala Lys Asp Arg Ser Glu
        195                 200                 205
Glu Glu Arg Thr Thr Glu Ala Glu Lys Asn Glu Arg Val Gln Lys His
    210                 215                 220
Leu Lys Ala Leu Thr Ser Glu Leu Ala Asn Ala Arg Asp Glu Ser Lys
225                 230                 235                 240
Lys Thr Ala Asn Asp Met Ile His Ala Glu Asn Met Arg Leu Gly Arg
                245                 250                 255
Asp Lys Tyr Lys Thr Leu Arg Gln Ile Arg Gln Gly Asn Thr Lys Gln
            260                 265                 270
Arg Ile Asp Glu Phe Glu Ser Met
        275                 280

<210> SEQ ID NO 4
<211> LENGTH: 173
<212> TYPE: PRT
<213> ORGANISM: Artificial
<220> FEATURE:
<223> OTHER INFORMATION: helical domain of human moesin protein

<400> SEQUENCE: 4

Asp Thr Ile Glu Val Gln Gln Met Lys Ala Gln Ala Arg Glu Glu Lys
1               5                   10                  15
His Gln Lys Gln Met Glu Arg Ala Met Leu Glu Asn Glu Lys Lys Lys
            20                  25                  30
Arg Glu Met Ala Glu Lys Glu Lys Glu Lys Ile Glu Arg Glu Lys Glu
        35                  40                  45
Glu Leu Met Glu Arg Leu Lys Gln Ile Glu Glu Gln Thr Lys Lys Ala
    50                  55                  60
Gln Gln Glu Leu Glu Glu Gln Thr Arg Arg Ala Leu Glu Leu Glu Gln
65                  70                  75                  80
Glu Arg Lys Arg Ala Gln Ser Glu Ala Glu Lys Leu Ala Lys Glu Arg
                85                  90                  95
Gln Glu Ala Glu Glu Ala Lys Glu Ala Leu Leu Gln Ala Ser Arg Asp
            100                 105                 110
Gln Lys Lys Thr Gln Glu Gln Leu Ala Leu Glu Met Ala Glu Leu Thr
        115                 120                 125
Ala Arg Ile Ser Gln Leu Glu Met Ala Arg Gln Lys Lys Glu Ser Glu
    130                 135                 140
Ala Val Glu Trp Gln Gln Lys Ala Gln Met Val Gln Glu Asp Leu Glu
145                 150                 155                 160
```

Lys Thr Arg Ala Glu Leu Lys Thr Ala Met Ser Thr Pro
            165                 170

<210> SEQ ID NO 5
<211> LENGTH: 107
<212> TYPE: PRT
<213> ORGANISM: Artificial
<220> FEATURE:
<223> OTHER INFORMATION: C-terminal tail domain of human moesin protein

<400> SEQUENCE: 5

His Val Ala Glu Pro Ala Glu Asn Glu Gln Asp Glu Gln Asp Glu Asn
1               5                   10                  15

Gly Ala Glu Ala Ser Ala Asp Leu Arg Ala Asp Ala Met Ala Lys Asp
            20                  25                  30

Arg Ser Glu Glu Glu Arg Thr Thr Glu Ala Glu Lys Asn Glu Arg Val
        35                  40                  45

Gln Lys His Leu Lys Ala Leu Thr Ser Glu Leu Ala Asn Ala Arg Asp
    50                  55                  60

Glu Ser Lys Lys Thr Ala Asn Asp Met Ile His Ala Glu Asn Met Arg
65                  70                  75                  80

Leu Gly Arg Asp Lys Tyr Lys Thr Leu Arg Gln Ile Arg Gln Gly Asn
                85                  90                  95

Thr Lys Gln Arg Ile Asp Glu Phe Glu Ser Met
            100                 105

<210> SEQ ID NO 6
<211> LENGTH: 1734
<212> TYPE: DNA
<213> ORGANISM: Artificial
<220> FEATURE:
<223> OTHER INFORMATION: cDNA Sequence encoding for the Full Length
      Human Moesin Protein

<400> SEQUENCE: 6
atgcccaaaa cgatcagtgt gcgtgtgacc accatggatg cagagctgga gtttgccatc      60
cagcccaaca ccaccgggaa gcagctattt gaccaggtgg tgaaaactat tggcttgagg     120
gaagtttggt tctttggtct gcagtaccag gacactaaag gtttctccac ctggctgaaa     180
ctcaataaga aggtgactgc ccaggatgtg cggaaggaaa gccccctgct ctttaagttc     240
cgtgccaagt tctaccctga ggatgtgtcc gaggaattga ttcaggacat cactcagcgc     300
ctgttctttc tgcaagtgaa agagggcatt ctcaatgatg atatttactg cccgcctgag     360
accgctgtgc tgctggcctc gtatgctgtc cagtctaagt atggcgactt caataaggaa     420
gtgcataagt ctggctacct ggccggagac aagttgctcc gcagagagt cctggaacag     480 cacaaactca acaaggacca gtgggaggag cggatccagg tgtggcatga ggaacaccgt     540
ggcatgctca gggaggatgc tgtcctggaa tatctgaaga ttgctcaaga tctggagatg     600
tatggtgtga actacttcag catcaagaac aagaaaggct cagagctgtg gctgggggtg     660
gatgccctgg gtctcaacat ctatgagcag aatgacagac taactcccaa gataggcttc     720
ccctggagtg aaatcaggaa catctctttc aatgataaga aatttgtcat caagcccatt     780
gacaaaaaag ccccggactt cgtcttctat gctccccggc tgcggattaa caagcggatc     840
ttggccttgt gcatggggaa ccatgaacta tacatgcgcc gtcgcaagcc tgataccatt     900
gaggtgcagc agatgaaggc acaggccagg gaggagaagc accagaagca gatggagcgt     960
gctatgctgg aaaatgagaa gaagaagcgt gaaatggcag agaaggagaa agagaagatt    1020

-continued

```
gaacgggaga aggaggagct gatggagagg ctgaagcaga tcgaggaaca gactaagaag    1080
gctcagcaag aactggaaga acagacccgt agggctctgg aacttgagca ggaacggaag    1140
cgtgcccaga gcgaggctga aaagctggcc aaggagcgtc aagaagctga agaggccaag    1200
gaggccttgc tgcaggcctc ccgggaccag aaaaagactc aggaacagct ggccttggaa    1260
atggcagagc tgacagctcg aatctcccag ctggagatgg cccgacagaa gaaggagagt    1320
gaggctgtgg agtggcagca gaaggcccag atggtacagg aagacttgga gaagacccgt    1380
gctgagctga agactgccat gagtacacct catgtggcag agcctgctga gaatgagcag    1440
gatgagcagg atgagaatgg ggcagaggct agtgctgacc tacgggctga tgctatggcc    1500
aaggaccgca gtgaggagga acgtaccact gaggcagaga agaatgagcg tgtgcagaag    1560
cacctgaagg ccctcacttc ggagctggcc aatgccagag atgagtccaa gaagactgcc    1620
aatgacatga tccatgctga gaacatgcga ctgggccgag acaaatacaa gaccctgcgc    1680
cagatccggc agggcaacac caagcagcgc attgacgaat ttgagtctat gtaa          1734
```